United States Patent [19]

Hejna et al.

[11] Patent Number: 5,863,751
[45] Date of Patent: Jan. 26, 1999

[54] ADDITION OF LACTOSE OR OTHER SUGARS IN CORRECTING FALSE SUSCEPTIBILITY RESULTS FOR RESISTANT MICROORGANISMS IN ANTIMICROBIAL SUSCEPTIBILITY TESTS

[75] Inventors: John M. Hejna, Reisterstown; Gertrude M. Karr, Baltimore; Denise R. Holliday, Laurel; William B. Brasso, Columbia; Patricia Hammond, Parkton, all of Md.

[73] Assignee: Becton Dickinson and Company, Franklin Lakes, N.J.

[21] Appl. No.: 724,487

[22] Filed: Sep. 30, 1996

[51] Int. Cl.$^6$ ........................................................ C12Q 1/18
[52] U.S. Cl. .................................. 435/32; 435/29; 435/30
[58] Field of Search .................................. 435/29, 30, 32, 435/33, 34, 243; 424/114

[56] References Cited

U.S. PATENT DOCUMENTS

| | | | |
|---|---|---|---|
| 5,164,301 | 11/1992 | Thompson et al. | 435/29 |
| 5,457,030 | 10/1995 | Badal et al. | 435/34 |
| 5,563,043 | 10/1996 | Schalkowsky et al. | 435/32 |
| 5,567,598 | 10/1996 | Stitt et al. | 435/29 |
| 5,627,045 | 5/1997 | Bochner et al. | 435/34 |

*Primary Examiner*—Ralph Gitomer
*Attorney, Agent, or Firm*—Bruce S. Weintraub

[57] ABSTRACT

The present invention relates to a method for correcting false susceptibility results in antimicrobial susceptibility tests for resistant microorganisms. This method comprises adding specific amounts of sugars, carbohydrates, related compounds or other ingredients to a test medium for such susceptibility tests.

6 Claims, No Drawings

ADDITION OF LACTOSE OR OTHER SUGARS IN CORRECTING FALSE SUSCEPTIBILITY RESULTS FOR RESISTANT MICROORGANISMS IN ANTIMICROBIAL SUSCEPTIBILITY TESTS

FIELD OF THE INVENTION

The present invention is directed to a method for correcting false susceptibility results in Antimicrobial Susceptibility Tests (AST) for resistant microorganisms, comprising adding specific amounts of lactose or other sugars, and if necessary other ingredients, in a test solution for the AST.

BACKGROUND OF THE INVENTION

"Antimicrobial Susceptibility Tests" (AST) are performed to predict the therapeutic effectiveness of different antibiotics for the treatment of infections. The test is performed in vitro (outside the patient) using the microorganism cultivated from an infection site (i.e., wound, urine, stool, etc.). Although the AST method described in the present invention refers to testing bacteria, AST methods have also been developed for other infectious disease agents (such as viruses, fungi, parasites).

Bacterial AST testing is usually performed using a battery of antimicrobial agents. The results provided from this test allow the physician to select the most effective agent from a "menu" of antibiotic choices available. Since therapy is usually initiated before the infectious agent is cultivated, initial antibiotic therapy is selected empirically (i.e., based on the physician's presumptive diagnosis). Therefore, the AST results are, in practice, usually used only to modify therapy, particularly if the patient is not responding well to the initial therapeutic choice.

The most common AST performed today are the broth-dilution Minimum Inhibitory Concentration (MIC) method, and the disk diffusion method. An agar dilution method is also used to a lesser extent..

The broth-dilution method is performed by inoculating a broth growth medium (usually Mueller Hinton Broth) with an organism at a standard density (about $3-7 \times 10^5$ bacterial cells/milliliter). The broth suspension is then separated into aliquots (usually 0.1 ml) in wells containing antibiotics in a microdilution panel. A series of wells (aliquots) are tested for each antibiotic with each well containing a progressively increasing concentration of drug. The antibiotic/microorganism mixtures are incubated at body temperature (35°–37° C.) for enough time to allow the organism to grow in a well without any antibiotic (growth control well). For inhibitory concentrations of antibiotic(s), no visible evidence of growth is observed after the incubation period. Whereas, growth will be observed in wells were the antibiotic concentrations are not inhibitory. The minimal amount of antibiotic (lowest concentration) needed to inhibit the growth of the organism (the MIC value) is an end point (parameter) used to quantitate the effectiveness of the antibiotic. Lower MIC values indicate more effective antibiotics.

The relative therapeutic effectiveness of the antibiotic is determined by comparing the MIC to the achievable levels of the antibiotic in the body following injection or other delivery methods to the patient. A general "rule of thumb" is that effective agents have an MIC at least 10 times lower than the peak serum level of the antibiotic. In practice, the MIC values are converted to a simpler qualitative result (susceptible, intermediate, or resistant) for the physician. These qualitative values are derived from tables developed by organizations such as the National Committee for Clinical Laboratory Standards (NCCLS).

Background publications on this test include: "Antimicrobial Susceptibility Testing: General Considerations "by James H. Jorgensen and Daniel F. Sahm, Ch. 110, pp. 1277–1280, in Manual of Clinical Microbiology, Sixth Edition, P. R. Murray et. al. eds., ASM Press, Washington D.C., 1995, and "Antibacterial Susceptibility Tests: Dilution and Diffusion Methods" by Gail L. Woods and John A. Washington, Ch. 113, pp. 1327–1341, in Manual of Clinical Microbiology, Sixth Edition, P. R. Murray et. al. eds., ASM Press, Washington, D.C. 1995. These references are incorporated herein by reference.

The Sceptor® MIC system is very similar to the microdilution method by NCCLS. "Sceptor® MIC panels" contain antimicrobial agents dried in an 84-well tray. Each panel has up to 83 wells containing antimicrobial agents and one growth control well. A bacterial suspension in Sceptor® broth medium is used for rehydration of the antimicrobial agents and biochemicals and inoculation of the wells. Following an incubation period, the wells containing the antimicrobial agents are viewed for bacterial growth. The least amount of an antimicrobial which results in no visible growth, is the MIC for that particular antimicrobial.

It had been found that Sceptor® MIC panels have been exhibiting false susceptibility results with certain resistant microorganisms, such as, for example, for two antimicrobics, Piperacillin and Aztreonam. This necessitated the removal of Piperacillin and Aztreonam from the Sceptor® panels until a solution for this inconsistency could be found.

The present invention describes a method for solving the problem described above by utilization of certain specific and heretofore unrevealed beneficial concentrations of sugars and/or other ingredients to prevent false susceptibility results in such AST.

SUMMARY OF THE INVENTION

The present invention relates to a method for correcting false susceptibility results in AST for resistant microorganisms, comprising adding specific amounts of lactose or other sugars and/or other ingredients including carbohydrates to a test solution for the AST.

DETAILED DESCRIPTION OF THE INVENTION

The present invention is directed to a method for correcting false susceptibility results in AST for resistant microorganisms.

The AST referred to herein is the broth dilution MIC method discussed in the above "Background of the Invention." The present invention encompasses the "β-Lactam" class of antibiotics and more, particularly, in one embodiment, those having utility against gram-negative organisms. Some of the β-Lactam class includes the following sub-groups: cephalosporins, penicillins, monobactams and carbapenems. In a preferred embodiment, the antibiotics to be evaluated can include: Aztreonam, Ceftazidime, Piperacillin, Mezlocillin, and Ticarcillin. All of these agents, when previously tested in the Sceptor® system were found to have varying degrees of difficulty in detecting resistant gram negative bacterial strains. All of the above antibiotics will show improved resistance detection when sugars are used in the test solution.

In addition, some of the above drugs can be combined with β-Lactamase inhibitors (such as, for example, Clavulanic acid and Tazobactam). These "combination agents" (such as Piperacillin/Tazobactam—trade name Zosyn, and Ticarcillin/Clavulanic acid—trade name Timentin) will show improved detection of resistant organisms when sugars are also included with the antibiotics.

The present invention relates to a method for correcting false results in ASTs comprising adding a specific amount of sugars (monosaccharides and dissaccharides) to a final test solution for an AST.

In a preferred embodiment, the sugar can be a glycosidic carbohydrate. This can preferably include the following: lactose, dextrose, fructose, sorbitol and sucrose. Also included are other saccharides such as: adonitol, arabinose, dulcitol, galactose, inositol, maltose, mannitol, raffinose, roamnose, and trehalose The concentration range of the sugar or related compound can preferably be from about 0.1% to about 4%, and most preferably about 1% (grams/100 ml) to about 2%. In another preferred embodiment, the final test solution can have the above concentrations of a sugar or a related compound (from about 0.1% to about 4.9% and more preferably, from about 1% to about 2%) in combination with a lower antibiotic potency (about 70% to about 85%, and preferably from about 77% to about 82%). In another embodiment, the concentration of the sugar or other related compound can be the concentration at which osmotic pressure would start to inhibit bacterial growth (osmotic pressure would dehydrate the bacterium). This concentration is likely to be variable dependent on the organism. Most bacteria are inhibited at solution concentrations between 50%–70%; a few saccharophylic microorganisms can tolerate greater than 70% sucrose levels.

The following Examples are intended to be demonstrative in nature and are not intended to in any way limit the present invention.

EXAMPLES

Example I

The results of an AST in which specific concentrations of sugars/carbohydrates have been added to the test solution are set forth in Table I, Table II, and Table III below:

TABLE I

| | | MIC* | | |
|---|---|---|---|---|
| Sugars | Range | Aztreonam | Ceftazidime | Piperacillin |
| Organism: BDMS Culture No. 9916, Pseudomonas aeruginosa | | | | |
| Dextrose (Glucose) | 0% | 8,8,8 | 8,8,8 | 64,64,64 |
| | 0.5% | 8 | 8 | 64 |
| | 1% | 8 | 8 | 64 |
| | 2% | 16 | 32 | 128 |
| | 2.5% | 16,16,16 | 16,32,32 | 128,64,64 |
| | 3% | >=32 | 32 | 128 |
| | 4% | 16 | 32 | 128 |
| | 5% | 16,16,16 | 32,32,32 | 18,64,64 |
| Sucrose | 0% | 8 | | 64 |
| | 2.5% | 8 | | 64 |
| | 5% | >=32 | | 128 |
| Sorbitol | 0% | 8 | | 64 |
| | 2.5% | 16 | | 128 |
| | 5% | 32 | | 128 |
| Fructose | 0% | 8,8,8 | 8,8 | 64,64,64 |
| | 0.5% | 8 | 16 | 64 |
| | 1% | 8,8 | 16,8 | 64,64 |
| | 1.5% | 8 | 16 | 64 |
| | 2% | 8 | 16 | 64 |
| | 2.5% | 16 | | 128 |
| | 5% | 16 | | 128 |

TABLE I-continued

| | | MIC* | | |
|---|---|---|---|---|
| Sugars | Range | Aztreonam | Ceftazidime | Piperacillin |
| Lactose | 0% | 8,8,16,8,16,8 | 8,16,8 | 64,64,64 |
| | 1% | 16,32 | | |
| | 2.5% | 16,32,32,16,32,16 | 16,32,16 | 128,128 |
| | 5% | >=32,32,64,32 | 32 | 2.56 > 128 |
| Organism: CDC 2300 Pseudomonas aeruginosa | | | | |
| Sucrose | 0% | 8 | | 16 |
| | 2.5% | 8 | | 16 |
| | 5% | 16 | | 16 |
| Sorbitol | 0% | 8 | | 16 |
| | 2.5% | 8 | | 16 |
| | 5% | 8 | | 16 |
| Fructose | 0% | 8 | | 16 |
| | 2.5% | 8 | | 16 |
| | 5% | 8 | | 32 |
| Lactose | 0% | 8,8,8 | 4 | 16,16 |
| | 2.5% | 16,16 | 8 | 16 |
| | 5% | >=32 | | 16 |

*Concentration in mcg/ml in the well

TABLE II

Organism: ATCC 35029, Enterobacter aerogenes

| | | MIC | | |
|---|---|---|---|---|
| Sugars | Range | Aztreonam | Ceftazidime | Piperacillin |
| Dextrose (Glucose) | 0% | 16 | 16 | 32 |
| | 2.5% | 16 | 32 | 64 |
| | 5% | 16 | 32 | 64 |

TABLE III

Organism: ATCC 35030, Enterobacter cloacae

| | | MIC | | |
|---|---|---|---|---|
| Sugars | Range | Aztreonam | Ceftazidime | Piperacillin |
| Dextrose (Glucose) | 0% | <=4 | 16 | 128 |
| | 2.5% | 16 | 16 | >128 |
| | 5% | 8 | 32 | 128 |

Example II

Internal Equivalency

The Internal Equivalency study tested gram-negative and gram-positive bacterial isolates against the "Old" formulations (Solvent: water, Potency: 120%), and "New" modified antimicrobic formulations (Solvent: 1% Lactose, Potency: 80%) contained in a single experimental panel. Each strain was also tested in an NCCLS microdilution reference panel. The data derived from the gram-negative strains were evaluated for all three antimicrobics, whereas the data from the gram-positive strains were analyzed only for piperacillin and ceftazidime. (Aztreonam shows little or no activity for gram-positives, and is not used for MIC testing in any current Sceptor® gram-positive panels).

In the Internal Equivalency Studies, the number of False Susceptible Errors was reduced by the addition of Lactose and the reduction of potency of the antibiotic. If False Susceptible results are used to predict susceptibility of the microorganism to the drug, treatment with an inappropriate drug could result. False Resistant Errors were not significantly changed by the new formulation. In addition to the data shown below in Table IV, similar experiments were conducted using Ticarcillin/Clavulanic Acid and Mezlocillin (results not shown). Similar results were obtained.

TABLE IV

| Drug | Susceptible Strains (#) | % False Resistant[1] | Resistant Strains (#) | % False Susceptible[2] |
|---|---|---|---|---|
| Ceftazidime | 213 (New) | 1.5% (New) | 123 (New) | 1% (New) |
| " | 213 (Old) | 0.5% (Old) | 123 (Old) | 4.1% (Old) |
| Aztreonam | 112 (New) | 0% (New) | 114 (New) | 1.7% (New) |
| " | 112 (Old) | 0% (Old) | 113 (Old) | 13.3% (Old) |
| Piperacillin/ Tazobactam | 263 (New) | 0.4% (New) | 106 (New) | 9.4% (New) |
| Piperacillin/ Tazobactam | 263 (Old) | 0% (Old) | 106 (Old) | 28.3% (Old) |

(New) Formula: Solvent: 1% Lactose in water, Potency: 80%
(Old) Formula: Solvent: water, Potency: 120%
[1]False Resistant: Susceptible Strains which give a Resistant Result.
[2]False Susceptible: Resistant Strains which give a Susceptible Result

What we claim is:

1. In a method for correcting and preventing false susceptibility results in antimicrobial susceptibility tests for resistant microorganisms, by a broth microdilution method, comprising providing an improved testing medium in said microdilution method, wherein the improvement to said medium comprises addition of a sugar selected from the group consisting of lactose, dextrose, fructose, sorbitol, sucrose, adonitol, arabinose, dulcitol, galactose, inositol, maltose, mannitol, raffinose, rhamnose and trehalose in a concentration of from about 0.1% to about 4.9% in said testing medium.

2. The improvement of claim 1 wherein said sugar is in a concentration of from about 1% to about 2% in said testing medium.

3. The improvement of claim 1 which further comprises an antimicrobial or antibiotic with a lower antimicrobial or antibiotic potency than in a standard Antimicrobial Susceptibility Test from about 70 to 85% potency.

4. The improvement of claim 3, wherein said antimicrobial or antibiotic potency is from about 77% to about 82%.

5. The improvement of claim 3 further comprising addition of a beta-lactamase inhibitor in an amount sufficient to inhibit any beta-lactamase present.

6. The improvement of claim 1 further comprising addition of a beta-lactamase inhibitor in an amount sufficient to inhibit any beta-lactamase present.

* * * * *